United States Patent [19]

Chou

[11] Patent Number: 5,206,432

[45] Date of Patent: Apr. 27, 1993

[54] PROCESS FOR PREPARING MONOAMIDO ACIDS

[75] Inventor: Yueting Chou, Chesterfield, Mo.

[73] Assignee: Monsanto Company, St. Louis, Mo.

[21] Appl. No.: 920,717

[22] Filed: Jul. 28, 1992

[51] Int. Cl.$^5$ ............................................ C07C 205/00
[52] U.S. Cl. ..................................... 562/553; 562/450
[58] Field of Search ................................ 562/553, 450

[56] References Cited

U.S. PATENT DOCUMENTS

| | | | |
|---|---|---|---|
| 2,191,738 | 9/1934 | Balle | 260/534 |
| 2,371,104 | 3/1945 | Kienle et al. | 3/70 |
| 2,502,478 | 2/1947 | Padbury et al. | 260/482 |
| 2,604,449 | 7/1952 | Bryant et al. | 252/33.6 |
| 4,681,592 | 7/1987 | Hardy et al. | 8/111 |
| 4,686,063 | 8/1987 | Burns | 252/102 |
| 5,117,058 | 5/1992 | Chen et al. | 564/157 |

FOREIGN PATENT DOCUMENTS 1468860 6/1989 Fed. Rep. of Germany .
3624057 12/1961 Japan .

*Primary Examiner*—Michael L. Shippen
*Attorney, Agent, or Firm*—R. C. Loyer

[57] ABSTRACT

There is disclosed a novel process of preparing highly pure monoamido acid by the reaction of a dibasic acid and an amine wherein a large molar excess of dibasic acid is utilized and conveniently recovered for recycle in the process to prepare additional amounts of the said monoamido acid. It has been discovered that amidation of both acid groups of the dibasic acid is held to low levels while efficiency of the reaction is maintained by recycle of unreacted starting acid. The unwanted diamido compound is separated from the desired product by first forming a water soluble salt of the monoamido acid then removing it from the insoluble diamido by-product by conventional means such as filtration. The desired monoamido acid may be recovered by acidification of the salt thereby precipitating the acid for easy recovery from an aqueous medium.

28 Claims, 2 Drawing Sheets

PROCESS FOR PREPARING MONOAMIDO ACIDS

This invention relates to the preparation of monoamido acids by the reaction of an amine with a dibasic acid wherein excessive amounts of N,N'-disubstituted diamide (diamides) avoided.

BACKGROUND OF THE INVENTION

The reaction of amines with polycarboxylic acids such as dibasic acids has long been known and takes place spontaneously at elevated temperatures with the evolution of water. As previously practiced, the second carboxyl group of the dibasic acid can react with the amine reactant such that a large amount of the amine is taken up by the amidation of both carboxyl groups of the dibasic acid thereby providing a mixture of monoamido carboxylic acid and N,N'-disubstituted diamide. A typical example of such a reaction is found in U.S. Pat. No. 2,604,449 to Bryant et al wherein amines are reacted with dibasic acids such as itaconic acid, adipic acid, succinic acid, azelaic acid, sebacic acid, and malonic acid. Approximately equal molar amounts of dibasic acids are shown to react with primary or secondary amines. The resulting reaction product is incorporated into lubricant compositions or greases for industrial purposes. Such purposes do not require high purity and therefore no accounting for the formation of diamide compounds was made.

Previously it was known to prepare monoamido derivatives of polycarboxylic acids by reacting the anhydride or esterified form of the polycarboxylic acid with an amine, obtaining an amido ester and then saponifying the ester group to provide a monoamido carboxylic acid. Such a process is disclosed in U.S. Pat. No. 2,191,738 to Balle. It is noted therein that the condensation of amines with polycarboxylic acids may be carried out by simply heating the two components with an excess of the acid deriviative until the reaction is complete. While no recognition of the formation of diamide and polyamide compounds is made, there is reference to the removal of insoluble byproducts in the examples.

A recent patent, U.S. Pat. No. 4,634,551 to Burns et al, describes novel, relatively stable and high melting crystalline amide peracids generically described as fatty peroxyacids having amide moieties in the fatty chain. An important feature of these compounds, as well as any other peracid, is their high purity, i.e., the absence of any impurities such as N'N'-disubstituted diamides in the case of amide peracids. Generally, the precursors of these amide peracids, that is, the amide acids, were reported to have been prepared by the reaction of the appropriate acid chloride with the appropriate amine followed by precipitation of the resulting amido acid. These compounds are said to have utility in detergent compositions as bleaching agents. The use of said compounds in detergent compositions requires large amounts of highly purified precursor materials from which the amide peracids may be prepared.

There is therefore needed a convenient, efficient process for the preparation of large amounts of monoamido acids in such high degree of purity, that amide peracids may be prepared which are stable and useful in detergent compositions. However, in the experience of the present inventor, it has been found that the known reactions of amines with polycarboxylic acids results in the production of large amounts of diamide and polyamide compounds rendering the process relatively inefficient. Several attempts to prepare monoamido polycarboxylic acids through derivatives of the acid have resulted in some refinements such as is described in co-pending application Ser. No. 826,555, filed Jan. 27, 1992 to Alul et al. The process of Alul et al, while found to be fairly efficient by means of the use of catalysts, employs as a starting material a diester of a dibasic acid, which is reacted with an akyl amine to produce the monoamido ester which is purified by distillation. To provide peroxy carboxylic acids, there is then required the hydrolysis of the other ester group. These reactions produce by-product alcohols and the need for purification of the disclosed monoamido carboxylic acid through acidification and filtration.

There is needed a direct process for producing the monoamido acid from the reaction of an amine and a dicarboxylic acid which avoids the production of large amounts of diamide compounds, as well as other byproducts.

BRIEF DESCRIPTION OF THE INVENTION

In accordance with this invention, there is provided a process or preparing precursors of fatty peroxyacids or salts thereof having amide moieties in the fatty chain. In one aspect of this invention, the above mentioned precursors are prepared by the direct reaction of a dibasic acid with an amine having at least one replaceable hydrogen on the nitrogen atom wherein the dibasic acid is present in the reaction mixture in large molar excess. As employed in the specification and claims the term "large molar excess" means a molar ratio of said acid of up to about 20:1 with respect to the amine. In order to provide an efficient reaction, means have been found to conveniently recover and recycle the unreacted dibasic acid. Such means is the discovery that the dibasic acid can be easily dissolved in water, at elevated temperature whereas the desired monoamido acid and the diamide compound are insoluble.

In a preferred embodiment, the aqueous solution containing the unreacted dibasic acid is treated so as to precipitate the acid which is then dried and recycled in the process to prepare further monoamido acid. Likewise, the water employed to dissolve the dibasic acid can be recycled to dissolve further amounts of dibasic acid from further batches of the reaction mixture.

The monoamido acid is separated from the diamide unavoidably produced in minor amounts in the reaction by any one of various means. In a preferred embodiment, the solid residue of the reaction mixture, after removal of the excess dibasic acid, is combined with a basic aqueous solution whereby a water soluble salt of monoamido acid forms and dissolves in the solution. The diamide compound is insoluble in said basic solution and is separated from the solution by any conventional means. The desired monoamido acid is then provided by acidifying the basic aqueous solution thereby precipitating the desired amide acid which is recovered.

It has been discovered that the above described method provides an efficient process for the production of highly pure monoamido dibasic acid highly suitable for use as a precursor in the production of monoamido percarboxylic acid. The percarboxylic acid is provided by conventional means such as by peroxidation of the precursor acid.

DETAILED DESCRIPTION OF THE INVENTION

Figure 1:
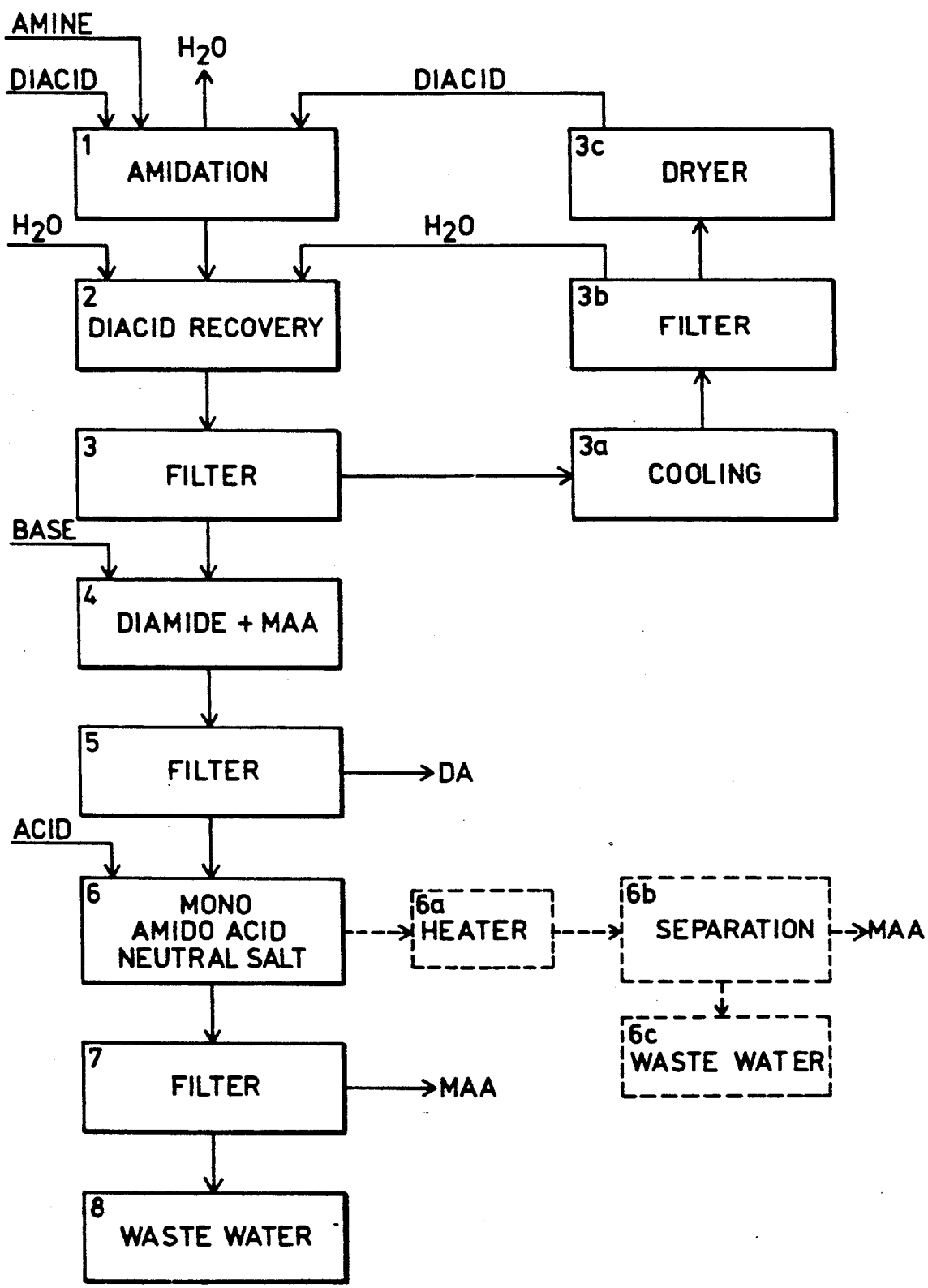
In FIG. 1 there is shown a flow diagram of the preferred embodiment of this invention.

The amidation reaction of the presently disclosed process takes place spontaneously at elevated temperatures in the range of from about 150° C. to about 200° C. Temperatures may be employed which are above the melting point of the dibasic acid and below the boiling point of the amine reactant. At such elevated temperatures, the dibasic acid reactant becomes liquid and readily reacts with the amine while also acting as a convenient reaction medium.

To suppress the formation of diamide, there is employed a large molar excess of the acid. It has been found that the larger the excess, the higher the selectivity to monoamido dibasic acid. For example, a molar ratio of dibasic to amine in the range of from about 3:1 to about 20:1 is employed and a molar ratio in the range of from about 5:1 to about 12:1 is preferred. Actually, any amount of excess dibasic acid to amine may be employed and is limited only by equipment size and working capacity desired. Because the reaction takes place at elevated temperatures, preferably in the range of from 155° C. to about 175° C. for adipic acid, a preferred embodiment, extremely large volumes are energy inefficient. Accordingly, a preferred molar ratio of adipic acid to amine is about 8:1.

In addition to the preferred adipic acid, any number of other dibasic acids can be employed in the process of this invention. The commonly available dibasic acids are, for example, glutaric acid, malonic acid, oxalic acid, succinic acid, itaconic acid, azelaic acid, sebacic acid, dodecanoic acid and others.

Typical amines employed to amidate the dibasic acid in accordance with this invention may be either primary or secondary amines and include, preferably alkyl amines, such as n-butylamine, n-hexylamine, n-heptylamine, octylamine, n-nonylamine, decylamine, laurylamine, stearylamine, monooleylamine, 2-ethylhexyl amine, dialkyl amines of the type listed above as primary amines, aryl amines and mixtures thereof. The above listed acids and amines are exemplary only and are not intended to be exclusive of other useful acids and amines in the process of this invention.

The reaction of the dibasic acid and amine takes place over a period of about 3 hours with thermal input. It is preferred to add the amine to the reactor after fusion of the dibasic acid reactant. It is preferred to exclude oxygen from the reactor by means such as purging the reactor with nitrogen, most preferably introduced subsurface in the reactor. Water is given off and is removed through a distillation head fitted on the top of the reactor. At the end of the reaction, as indicated by the termination of water removal, the reaction mixture is placed in water at an elevated temperature. For adipic acid as an example, the water temperature is in the range of from about 50° C. to about 95° C. At such temperature, the excess unreacted dibasic acid, dissolves in the hot water while the desired monoamido adipic acid and the unavoidably produced diamide precipitate and are removed from the acid solution by conventional means such as filtration. Typical filtration means includes plate and frame filters, centrifuge, or drum filters with vacuum assist. The filtrate containing the dibasic acid is then cooled thereby precipitating the acid which is then easily removed by filtration or any other conventional means. The filtrate (water) from this operation can then be recycled to dissolve further amounts of dibasic acid from the reactor while the dibasic acid is dried to remove excess free moisture and returned to the reactor for the production of further mono amido adipic acid.

By employing these recycle streams, it can be seen that large amounts of dibasic acid are employed without lowering the efficiency of the reaction since it, and its solvent water, are nearly quantitatively recovered and recycled. In a highly efficient mode of operation, the water removed from the reaction mixture of the dibasic acid and amine, as well as the excess water removed from the recycled dibasic acid, can be employed as make-up water to dissolve the dibasic acid from the reaction mixture in the second step of the process. The above noted water sources may also be employed to wash filter cake in various steps of the process.

The precipitated monoamido acid, together with the by-product diamide obtained by filtration of the dibasic acid solution, is then treated to separate the desired acid from the diamide. In a preferred embodiment, the precipitate is combined with a caustic solution whereupon the salt of monoamido adipic acid is formed and dissolves the diamide compound remains insoluble thereby allowing easy separation such as by filtration devices as noted above.

In an alternative embodiment, the precipitate obtained from the dibasic acid solution can be added to an organic solvent whereupon only the monoamido adipic acid dissolves allowing, again, for separation of the solution of the desired acid from the diamide compound followed by removal of the solvent and recovery of the desired acid. As an example, solvents for the monoamido adipic acid include acetic acid, DMF (N,N-dimethylformamide), sulfuric acid, said solvents having been slightly diluted with water. The diluted solvent has been found to minimize the dissolution of the diamide.

In the preferred embodiment, any basic material can be employed to provide the salt of the monoamido acid. Typical examples of bases which can be employed are alkali metal bases, alkaline earth metal bases, and tertiary amines. Preferably, alkali metal bases such as the alkali metal hydroxides or carbonates are employed. More preferably, sodium hydroxide is employed as a base to produce the sodium salt of monoamido acid. Other bases include potassium hydroxide, lithium hydroxide, cesium hydroxide, calcium hydroxide, magnesium hydroxide, sodium carbonate, calcium carbonate, potassium carbonate, or organic amines containing from 1 to 18 carbon atoms and no replacable hydrogens on the nitrogen where said organic amine is selected from the group consisting of trialkylammonium, trialkenylammonium and trialkynylammonium. Typical organic ammonium salts include trimethylamine, triethylamine, tri-n-propylamine, triisopropylamine, tri-n-butylamine, triisobutylamine, tri-sec-butylamine, tri-n-amylamine, and pyridine.

With the monoamido acid salt in solution, the undesired diamide is easily separated as noted above and in the case of filtration, the filtrate is then recovered containing the amide salt.

The solution containing the inorganic salt is acidified thereby restoring the monoamido adipic acid which precipitates in the aqueous medium leaving a neutral salt in solution. In this preferred embodiment, the desired amide acid is then separated from the aqueous medium by the usual conventional means such as filtration as noted above.

Alternatively, the precipitated acid may be separated from the aqueous medium by heating the aqueous medium whereby the amide acid precipitate liquifies forming two liquid phases. The amide acid is then recovered by liquid-liquid phase separation such as by means of a settler, providing highly pure mono amidio acid leaving only water as a residue.

Alternatively, the solution containing the tertiary amine salt is steam stripped to recover the amine and precipitate the desired mono amido acid.

In another embodiment, the amide acid precipitate may be recovered by employing an organic solvent for the amide acid thereby dissolving the amide acid leaving the diamide as an insoluble. The insoluble diamide is filtered off after which the solvent is removed from the monoamido acid. In this embodiment, the organic solvent may be added to the precipitate recovered after removal of the unreacted dibasic acid thereby avoiding the need for converting the acid to its salt for separation from the undesired diamide. The organic solvent, after recovery of the desired amide acid, may be recycled to the system thereby avoiding a waste product.

DETAILED DESCRIPTION OF THE DRAWINGS

In FIG. 1 there is shown a flow diagram showing the preferred embodiment of the process of this invention. In the first step, from the top of the diagram, dibasic acid and amine are reacted with the removal of water to provide amidation in the presence of a large excess of dibasic acid. The reaction mixture from step 1 is placed in an acid recovery vessel wherein water is added to dissolve the unreacted dibasic acid. The desired monoamido acid as well as a small amount of unavoidable diamide are not soluble in the heated water thereby making separation routine through means such as filtration shown in step 3.

The filtrate from step 3, containing unreacted dibasic acid is then cooled in step 3a allowing the dibasic acid to precipitate. The water used to dissolve the dibasic acid is recovered in step 3b as the filtrate and returned to step 2. The filter cake, containing a small amount of monoamido acid is dried to remove residual free water and then returned to the amidation reaction of step 1.

The filter cake produced in step 3 contains the desired monoamido acid (MAA) as well as a small amount of the diamide unavoidably produced in the amidation reaction of step 1. This filter cake is placed in an aqueous solution containing a base in step 4 whereby a salt of the monoamido acid is formed. The salt dissolves in the solution while the diamide remains solid. The monoamido acid salt in solution is isolated from the solid diamide by filtration in step 5 wherein the diamide is indicated in FIG. 1 as DA.

To obtain the desired monoamido acid, the salt is combined with an acid in step 6. The monoamido acid is not soluble in the acidic solution and therefore precipitates and is isolated in step 7 by filtration, indicated in FIG. 1 as MAA. The process leaves the filtrate from step 7 for disposal as waste water containing a neutral salt in step 8.

An alternative embodiment is shown in FIG. 1 by dotted lines. In this alternative embodiment the solid monoamido acid of step 6 is isolated by first heating the mixture of step 6 as shown in FIG. 1 by step 6a to liquify the solid monoamido acid. There is thus formed a separate organic layer comprising the monoamido acid. The two phase mixture is then separated in step 6b. The desired monoamido acid is obtained by typical liquid-liquid separation techniques. In FIG. 1 step 6b is indicated as a settling tank which provides means for separating the two liquid phases. This leaves an aqueous solution of neutral salt for disposal in step 6c.

Figure 2:
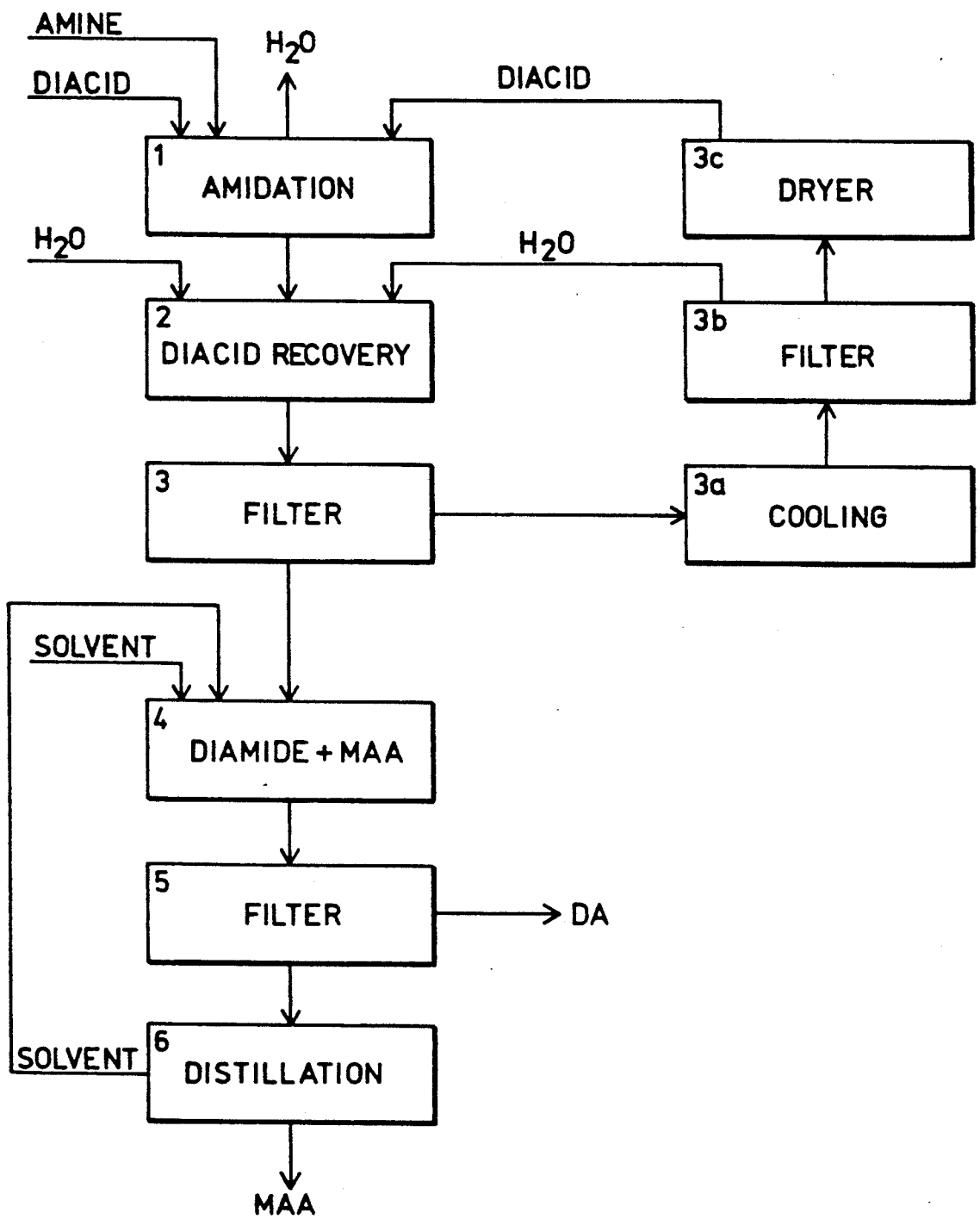
In FIG. 2 there is shown a flow diagram of an alternative embodiment of the process of this invention.

In FIG. 2 there is shown an alternative embodiment of the process of this invention. Steps 1 and 2 are the same as shown is FIG. 1 and described above with respect to FIG. 1. However, in step 3, the filter cake from step 2, containing the desired monoamido acid and the diamide are treated with a solvent which dissolves the monoamido acid leaving the diamide as a solid. The solid is filtered off in step 4 as indicated in FIG. 2 by DA and the filtrate is then removed by conventional means such as distillation in step 5 to provide amido acid indicated in FIG. 2 as MAA. In a preferred embodiment, the solvent is recovered and recycled in the process to dissolve further amounts of amido acid.

Description of the Preferred Embodiments

EXAMPLE ONE (Prior Art)

This example demonstrates the usual result obtained by using equal molar ratios of adipic acid and nonyl amine whereby most of the amine is employed in producing N,N'-dinonyl adipamide rather than the desired monoamido adipic acid.

Into a 500 ml, 4-neck round bottom flask, equipped with an overhead mechanical stirrer, a thermometer, and a straight takeover distillation head were added 146.2 g (1 mole) of adipic acid. The adipic acid was heated to 160° C. with agitation to form a melt. Then 143.3 g (1 mole) nonylamine was added to the flask over a period of 2.5 hours without agitation. The reaction mixture was held at a temperature in the range of from about 155° C. to 160° C. for an additional 3 hours without agitation. However, the evolution of water from the reaction created adequate agitation. A sample of the reaction product was subjected to melting point determination and the melting point range was found to be from 92° C. to 122° C. The hot reaction mixture was poured into a caustic solution (76.53 g of 50% sodium hydroxide and 1,594 ml of water) at 70° C. The N,N'-dinonyl adipamide was removed by filtration and dried in an oven at 70° C. overnight. The alkaline solution was then acidified with concetrated sulfuric acid (49.4 g) and 319 ml of water to precipitate monoamido adipic acid. The acid was collected by filtration and dried in an oven. About 108.5 g (0.4 mole) of acid was obtained. After drying, about 112.75 g (0.29 moles) of N,N'-dinonyl adipamide was obtained. This shows that a total of about 0.6 moles of amine were taken up with the undesired N,N'-dinonyl adipamide, while only 0.4 mole of amine was taken up with the desired monoamido acid.

EXAMPLE 2

This example demonstrates the highly efficient process of the present invention.

Into a 1 L flask equipped as described as above in Example 1 were added 350.9 grams (2.4 moles) of adipic acid. This acid was heated to 160° C. with agitation until melted. After all of the adipic acid was melted, there were added 28.6 g (0.2 mole) of nonylamine over a period of about 15 minutes. The reaction mixture was held at 170° C. with agitation for an additional 3 hours under nitrogen. The reaction mixture was then gradually poured into 2 L of hot (70° C.) water, with agitation to dissolve the unreacted adipic acid. The mixture was filtered and the wetcake was washed with hot water to obtain a mixture of monoamido adipic acid and $N,N^1$-dinonyl adipamide. The wetcake was reslurried in a caustic solution (16 g of 50% sodium hydroxide and 200 g of water) whereby the acid dissolved leaving the insoluble N,N'-dinonyl adipamide as an insoluble which was removed by filtration. After drying overnight at 70° C., the amount of dinonyl amido adipamide was found to be 1.78 g (0.0045 mole). This amount of diamide represents a molar selectivity of 4.5% based upon the amine reactant. The alkaline solution was then acidified with an equivalent of sulfuric acid to precipitate the desired monoamido adipic acid which precipitated and was collected by filtration. After drying in an oven overnight at 70° C., the amount of monoamido adipic acid obtained was found to be 49 g (0.1808 mole) having a purity of 99.9% by HPLC. This amount of monoamido adipic acid represents a molar selectivity of 90% based upon the amine reactant. A sample of the acid was subjected to melting point determination which was found to be in the range of 108° C.-110° C. The filtrate containing dissolved adipic acid was cooled to room temperature, whereupon the adipic acid precipitated and was recovered by filtration. The solid collected from this filtration contained mostly adipic acid and a small amount of monoamido adipic acid. After removal of residual water, the adipic acid, containing small amounts of monoamido adipic acid, was ready to be used as starting material for further reaction with an amine. The filtrate obtained from the recovery of the adipic acid contained about 2% adipic acid and was used as the water source to dissolve further unreacted adipic acid from the next batch in the further production of monoamido adipic acid by the reaction of nonylamine with adipic acid.

Although the invention is described with respect to specific embodiments and modifications, the details thereof are not to be construed as limitations except to the extent indicated in the following claims.

What is claimed is:

1. A process for the preparing highly pure monoamido acid which comprises the steps of
   a. reacting a molten dibasic acid in large molar excess with a primary or secondary amine;
   b. combining the reaction mixture of step a. with water at an elevated temperature whereby the unreacted dibasic acid dissolves leaving a solid residue;
   c. separating the solid residue of b. from the dibasic acid solution;
   d. combining the solid residue from step c. with a basic aqueous solution whereby a water soluble salt of monoamido acid forms and dissolves in said solution and then separating the solution from any insoluble material; and,
   e. acidifying the separated solution of step
   d. thereby precipitating the monoamido acid and recovering said acid.

2. The process of claim 1 further including the step of cooling the solution recovered from step c. to precipitate unreacted dibasic acid, filtering the precipitate and returning the filtrate to step b.

3. The process of claim 2 wherein the precipitated dibasic acid is removed by filtration, dried and recycled to step a. of the process.

4. The process of claim 1 wherein the reaction of step a. is conducted at a temperature in the range of from about 150° C. to about 200° C.

5. The process of claim 4 wherein the temperature is in the range of from about 155° C. to about 175° C.

6. The process of claim 1 wherein the temperature of the solution of step b. is in the range of from about 50° C. to about 95° C.

7. The process of claim 1 wherein the basic solution of step d. is provided by a base selected from the group consisting of an alkali metal base, alkaline earth metal base, ammonium and organic amine base.

8. The process of claim 7 wherein the base is an alkali metal base.

9. The process of claim 8 wherein the alkali metal base is sodium hydroxide.

10. The process of claim 8 wherein the alkali metal base is a carbonate.

11. The process of claim 10 wherein the carbonate is sodium carbonate.

12. The process of claim 1 wherein the acidifying agent of step e. is an inorganic acid.

13. The process of claim 12 wherein the acid is sulfuric acid.

14. The process of claim 1 wherein the monoamido acid of step e. is recovered by filtration.

15. The process of claim 1 wherein the monoamido acid of step e. is recovered by heating the acidified mixture whereby two liquid phases form and then separating said liquid phases.

16. The process of claim 15 wherein the liquid phases are separated by means of a settling tank.

17. The process of claim 1 wherein the alkyl amine contains from 7 to 12 carbon atoms.

18. The process of claim 1 wherein the molar ratio of dibasic acid to said amine is in the range of from about 3:1 to about 20:1.

19. The process of claim 18 wherein the molar ratio is in the range of from about 5:1 to about 12:1.

20. The process for the preparing a monoamido acid which comprises the steps of
   a. reacting a molten dibasic acid in large molar excess with a primary or secondary amine;
   b. combining the reaction mixture of step a. with water at an elevated temperature whereby the unreacted dibasic acid dissolves leaving a solid residue;
   c. separating the solid residue from said acid solution;
   d. adding an organic solvent for said monoamido acid to the solid residue to dissolve said acid and separating the solution from the remaining solid, and;
   e. recovering said acid from solution by removal of said solvent.

21. A process for the preparing highly pure monoamido adipic acid which comprises the steps of
   a. reacting molten adipic acid in large molar excess with an alkyl primary or secondary amine;
   b. combining the reaction mixture of step a. with water at an elevated temperature whereby the unreacted adipic acid dissolves leaving a solid residue;
   c. separating the solid residue of b. from the adipic acid solution;
   d. combining the solid residue from step c. with a basic aqueous solution whereby a water soluble salt of monoamido adipic acid forms and dissolves in said solution and then separating the solution from any insoluble material; and, e. acidifying the solution of step d. thereby precipitating the monoamido adipic acid and recovering said acid.

22. The process of claim 21 wherein the alkyl amine is nonyl amine.

23. The process of claim 22 wherein the molar ratio of adipic acid to amine is in the range of from about 3:1 to about 20:1.

24. The process of claim 21 wherein monoamido adipic acid is recovered by filtration.

25. The process of claim 21 further including the steps of cooling the water solution of adipic acid of step b after removal of said solid residue whereby the adipic acid precipitates, separating and drying said precipitate to remove free moisture, then returning the dried precipitate to step a. and returning the water to step b.

26. The process of claim 21 wherein the monoamido acid of step e is recovered by heating the acidified mixture whereby two liquid phases form and then separating said liquid phases.

27. The process of claim 23 wherein the molar ratio of adipic acid to amine is about 8:1.

28. The process of claim 21 wherein the reaction temperature of step a is in the range of from about 155° C. to about 175° C.

* * * * *